United States Patent [19]

Massonneau et al.

[11] Patent Number: 4,925,951
[45] Date of Patent: May 15, 1990

[54] PROCESS FOR PREPARING 1-HYDROXYALKYL-2-METHYL-5-NITROIMIDAZOLES

[75] Inventors: Viviane Massonneau; Michel Mulhauser, both of Ecully; Albert Buforn, Lyon, all of France

[73] Assignee: Rhone-Poulenc Sante, Antony, France

[21] Appl. No.: 296,708

[22] Filed: Jan. 13, 1989

[30] Foreign Application Priority Data

Jan. 15, 1988 [FR] France .................................. 88 00417

[51] Int. Cl.$^5$ .................... C07D 233/94; C07D 405/06
[52] U.S. Cl. .................................... 548/338; 548/336; 548/339; 548/340
[58] Field of Search ................ 548/338, 336, 339, 340

[56] References Cited

PUBLICATIONS

*Chemical Abstracts*, 76:58380j(1972) [UK1,257,851, 12/22/71 (BASF)].
*Chemical Abstracts*, 77:139490t (1972) [D. Tomalia et al., *J. Heterocycl. Chem.* 1972, 9(4), 891–4].

*Primary Examiner*—Richard A. Schwartz
*Attorney, Agent, or Firm*—Stevens, Davis, Miller & Mosher

[57] ABSTRACT

Process for preparing 1-(hydroxyalkyl)nitroimidazoles of formula:

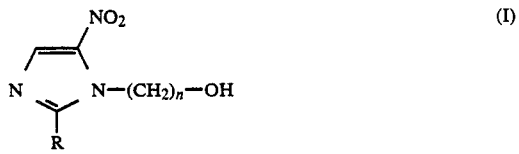

(I)

which comprises reacting a sulphite or diacetate of an alkylenediol of formula:

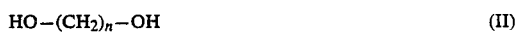

$$HO-(CH_2)_n-OH \quad \text{(II)}$$

in the presence of a strong acid (sulphuric acid) with an imidazole derivative of formula:

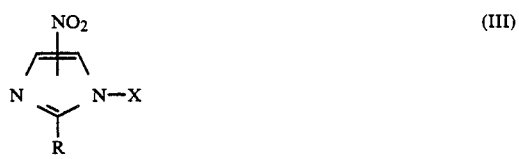

(III)

followed by hydrolizing or alcoholizing the product obtained. In the formulae (I) and (III), R denotes hydrogen or hydrocarbon. In the formulae (I) and (II), n is 2 or 3. In the formula (III), X denotes hydrogen or a radical which can be removed by hydrolysis or alcoholysis.

6 Claims, No Drawings

PROCESS FOR PREPARING 1-HYDROXYALKYL-2-METHYL-5-NITROIMIDAZOLES

The present invention relates to the preparation of 1-hydroxyalkyl-5-nitroimidazoles.

Among imidazole derivatives, 1-hydroxyethyl-2-methyl-5-nitroimidazole (or metronidazole), 1-(2-hydroxypropyl)-2-methyl-5-nitroimidazole (or secnidazole) or 1-(3-hydroxypropyl)-2-methyl-5-nitroimidazole (ternidazole) are of particular importance on account of their noteworthy therapeutic properties.

It is known to prepare metronidazole by the action of an excess of ethylene oxide on 2-methyl-4(or 5)-nitroimidazole under the conditions described in French Patent 1,379,915. However, the yields are not satisfactory.

It is known to prepare 2-(4-fluorophenyl)-1-hydroxymethyl-5-nitroimidazole by the action of ethylene sulphate on 2-(4-fluorophenyl)-4(or 5)-nitroimidazole according to the process described in U.S. Pat. No. 3,743,653. However, in this case, the yield is less than 10%.

According to the present invention, the 1-(hydroxyalkyl)-nitroimidazoles of formula:

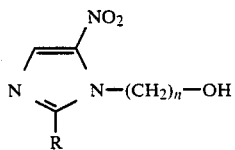

(I)

in which R denotes hydrogen, alkyl of 1 to 4 carbon atoms, or alkenyl of 2 to 4 carbon atoms, the said alkyl and alkenyl being unsubstituted or substituted by one or more identical or different radicals chosen from phenyl, phenoxy, and 5- or 6-membered oxygen-containing heterocyclic radicals, or alternatively R denotes aryl of 6 to 10 carbon atoms unsubstituted or substituted by one or more identical or different substituents chosen from halogen, alkyl of 1 to 4 carbon atoms, alkoxy of 1 to 4 carbon atoms, phenyl, phenoxy, and nitro, or alternatively R denotes cycloalkyl of 5 or 6 carbon atoms; the aforesaid phenyl, phenoxy and heterocyclic radicals being unsubstituted or substituted by one or more identical or different substituents chosen from halogen, alkyl of 1 to 4 carbon atoms, alkoxy of 1 to 4 carbon atoms, phenyl, phenoxy and nitro; and n is 2 or 3 and one of the carbon atoms of the alkylene chain $-(CH_2)_n-$ can be substituted by methyl, may be obtained in good yield by a process which comprises: reacting a sulphite or diacetate of an alkylenediol of formula:

$$HO-(CH_2)_n-OH \quad (II)$$

in which n is 2 or 3 and one of the carbon atoms of the alkylene chain $(CH_2)_n$ can be substituted by methyl in the presence of a strong acid, with an imidazole derivative of formula:

in which R is defined as above and X denotes hydrogen or a radical which can be removed by hydrolysis or alcoholysis, such as hydroxymethyl, alkoxymethyl of 1 to 4 carbon atoms or acyloxymethyl in which the acyl contains 1 to 4 carbon atoms in a straight or branched chain, or an allylic ethylenic radical such as allyl, or an arylmethyl such as benzyl; hydrolysing or alcoholysing the condensation product obtained; and isolating the 1-(hydroxyalkyl)nitroimidazole.

More especially, the rpesent invention relates to the preparation of 1-hydroxyethyl-2-methyl-5-nitroimidazole and 1-(2-hydroxypropyl)-2-methyl-5-nitroimidazole.

In general, the strong acid is sulphuric, methanesulphonic or p-toluenesulphonic acid.

The condensation is performed at a temperature from 80° to 140° C., and generally using one mole of acid and one mole of ester per mole of imidazole derivative of formula (III).

Moreover, when the diacetate of the alkylene glycol of formula (II) is used, it is especially advantageous to also use an acid anhydride, e.g., to use acetic anhydride and to distil off the acetic acid formed.

The condensation product may be dissolved:
either in an aqueous solution of a strong mineral acid, e.g. sulphuric acid or hydrochloric acid,
or in an alcohol such as, e.g., methanol or ethanol.

When the condensation product is dissolved in aqueous acid, the 1-(hydroxyalkyl)nitroimidazole is extracted according to the usual techniques after the pH of the reaction mixture has been adjusted to be in the region of 10.

When the condensation product is dissolved in an alcohol, the 1-(hydroxyalkyl)nitroimidazole is isolated according to the usual techniques without prior treatment of the reaction mixture.

When carrying out the process, it is not necessary to isolate the intermediate condensation product, and it is possible to perform the hydrolysis or alcoholysis sequentially in the same apparatus.

The imidazole derivative of formula (III) in which X denotes a hydroxymethyl, methoxymethyl, alkoxymethyl or acyloxymethyl radical may be prepared under the conditions described in British Patent 1,026,631.

The examples which follow show how the invention may be put into practice.

EXAMPLE 1

Ethylene sulphite (0.9 g; 0.0083 mole), 1-acetoxymethyl-2-methyl-4-nitroimidazole (0.2 g; 0.001 mole) and concentrated sulphuric acid (d=1.83) (60 micro-liters; 0.001 mole) are introduced into a round-bottomed flask equipped with a stirrer. The reaction mixture is heated to 120° C. for 4 hours. The hydrolysis is then carried out by adding a solution of sulphuric acid (60 microliters) in water (2 cc) and then heating the solution obtained to 90° C. for 8 hours.

After dilution of the reaction mixture, metronidazole (60 mg) is assayed by high performance liquid chromatography (HPLC) with external calibration.

The degree of conversion of 1-acetoxymethyl-2-methyl-4-nitroimidazole is 74%.

The yield of metronidazole is 35% relative to the 1-acetoxymethyl-2-methyl-4-nitroimidazole introduced and 47% relative to the 1-acetoxymethyl-2-methyl-4-nitroimidazole converted.

EXAMPLE 2

1-Acetoxymethyl-2-methyl-4-nitroimidazole (0.46 g; 0.0023 mole), glycol diacetate (2.5 cc) and concentrated sulphuric acid (d=1.83) (0.30 cc; 0.0028 mole) are introduced into a round-bottomed flask equipped with a stirrer. The reaction mixture is heated to 140° C. for 3 hours. The hydrolysis is then carried out by adding a solution of sulphuric acid (0.15 cc) in water (2.5 cc) and then heating the solution obtained to 80° C. for 4 hours.

After dilution, metronidazole (0.218 g) in the reaction mixture is assayed by HPLC with external calibration.

The degree of conversion of 1-acetoxymethyl-2-methyl-4-nitroimidazole is 92%.

The yield of metronidazole is 55% relative to the 1-acetoxymethyl-2-methyl-4-nitroimidazole introduced and 60% relative to the 1-acetoxymethyl-2-methyl-4-nitroimidazole converted.

EXAMPLE 3

2-Methyl-4(or 5)-nitroimidazole (0.334 g; 0.0026 mole), glycol diacetate (2.5 cc) and concentrated sulphuric acid (d=1.83) (0.15 cc; 0.0028 mole) are introduced into a round-bottomed flask equipped with a stirrer. The reaction mixture is heated to 140° C. for 3 hours. The hydrolysis is then carried out by adding a solution of sulphuric acid (0.15 cc) in water (2.5 cc) and then heating the solution obtained to 80° C. for 4 hours.

After dilution, metronidazole (185 mg) in the reaction mixture is assayed by HPLC with external calibration.

The degree of conversion of 2-methyl-4-(or 5)-nitroimidazole is 61%.

The yield of metronidazole is 41% relative to the 2-methyl-4-(or 5)-nitroimidazole introduced and 68% relative to the 2-methyl-4(or 5)-nitroimidazole converted.

EXAMPLE 4

Ethylene glycol diacetate (4.38 g; 0.03 mole), 1-acetoxymethyl-2-methyl-4-nitroimidazole (2 g; 0.02 mole), concentrated sulphuric acid (d=1.83) (1.56 g; 0.016 mole) and acetic anhydride (0.45 cc), for the purpose of removing the water present in the sulphuric acid, are introduced into a distillation apparatus in which the receiver is immersed in an acetone/dry ice bath. A pressure of 150 mmHg (20 kPa) is established in the apparatus, and the reaction mixture is then heated for 8 hours to 95° C. During the heating, acetic acid (0.94 g) is distilled off. The distillation apparatus is returned to atmospheric pressure and, after the reaction mass has been cooled, ethanol (15 cc) is added into the boiling vessel. The distillation apparatus is replaced by a condenser. The solution obtained after adding ethanol is heated under reflux for 4 hours.

After the mixture is cooled, metronidazole (1 g) in the reaction mixture is assayed by HPLC with external calibration.

The degree of conversion of 1-acetoxymethyl-2-methyl-4-nitroimidazole is 71%.

The yield of metronidazole is 59% relative to the 1-acetoxymethyl-2-methyl-4-nitroimidazole introduced and 83% relative to the 1-acetoxymethyl-2-methyl-4-nitroimidazole converted.

EXAMPLE 5

1-Acetoxymethyl-4-nitroimidazole (12 g; 0.06 mole), glycol diacetate (26 g; 0.18 mole) and concentrated sulphuric acid (9.4 g; 0.09 mole) are introduced into a round-bottomed flask equipped with a stirrer. The mixture is heated for 6 hours under a pressure of 150 mmHg (20 kPa). During the heating, a mixture of acetic acid and glycol diacetate is distilled off. Water (30 cc) is added and the mixture is then heated under reflux for 4 hours.

After dilution, assay by high performance liquid chromatography (HPLC) with external calibration shows that:

the degree of conversion of 1-acetoxymethyl-4-nitroimidazole is 87.8% the yield of 1-hydroxyethyl-5-nitroimidazole is 85% relative to the 1-acetoxymethyl-4-nitroimidazole converted.

We claim:

1. A process for preparing a 1-(hydroxyalkyl)nitroimidazole of formula:

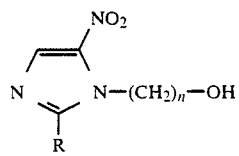

in which R denotes hydrogen, alkyl of 1 to 4 carbon atoms, or alkenyl of 2 to 4 carbon atoms, the said alkyl and alkenyl being unsubstituted or substituted by one or more identical or different radicals chosen from phenyl, phenoxy and 5- or 6-membered oxygen-containing heterocyclic radicals, or alternatively, R denotes aryl of 6 to 10 carbon atoms, unsubstituted or substituted by one or more identical or different substituents chosen from halogen, alkyl of 1 to 4 carbon atoms, alkoxy of 1 to 4 carbon atoms, phenyl, phenoxy and nitro, or alternatively R denotes cycloalkyl of 5 or 6 carbon atoms; the aforesaid phenyl, phenoxy and heterocyclic radicals being unsubstituted or substituted by one or more identical or different substituents chosen from halogen, alkyl of 1 to 4 carbon atoms, alkoxy of 1 to 4 carbon atoms, phenyl, phenoxy and nitro; and n is 2 or 3 and one of the carbon atoms of the alkylene chain —$(CH_2)_n$— can be substituted by methyl, which comprises reacting a sulphite or diacetate of an alkylenediol of formula:

in which n is 2 or 3 and one of the carbon atoms of the alkylene chain —$(CH_2)_n$— can be substituted by methyl at 80° to 140° C. with an imidazole derivative of formula:

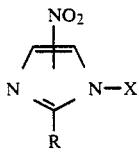

in which R is defined as above and X denotes hydrogen or a radical which can be removed by hydrolysis or alcoholysis, in the proportion of one mole of said sulphite or diacetate per mole of said imidazole derivative and in the presence of one mole of a strong acid per mole of said imidazole derivative; hydrolysing or alcoholysing the condensation product obtained and isolating the 1-(hydroxyalkyl)nitroimidazole derivative.

2. A process according to claim 1, wherein the group which can be removed by hydrolysis or alcoholysis is a hydroxymethyl radical, an alkoxymethyl radical in which the alkyl portion contains 1 to 4 carbon atoms, an acyloxymethyl radical in which the acyl portion contains 1 to 4 carbon atoms in a straight or branched chain, an allylic ethylenic radical, or an arylmethyl radical.

3. A process according to claim 1, wherein the strong acid is sulphuric, methanesulphonic or p-toluenesulphonic acid.

4. A process according to claim 1, wherein the hydrolysis of the condensation product is performed in the presence of sulphuric acid or hydrochloric acid.

5. A process according to claim 1, wherein the alcoholysis of the condensation product is performed by heating in the presence of methanol or ethanol.

6. A process according to claim 1, wherein the 1-(hydroxyalkyl)nitroimidazole obtained is metronidazole, secnidazole or ternidazole.

* * * * *